(12) United States Patent
Abbott et al.

(10) Patent No.: US 8,178,039 B2
(45) Date of Patent: May 15, 2012

(54) METHODS FOR CONTROLLING PERSPIRATION-RELATED BODY ODOR

(75) Inventors: Dominic C. Abbott, Pittsburg, PA (US); Chun Lim Abbott, Pittsburgh, PA (US)

(73) Assignee: Abbott Research Group, Inc., Philadelphia, PA (US)

( * ) Notice: Subject to any disclaimer, the term of this patent is extended or adjusted under 35 U.S.C. 154(b) by 0 days.

(21) Appl. No.: 13/116,334

(22) Filed: May 26, 2011

(65) Prior Publication Data

US 2011/0229370 A1 Sep. 22, 2011

Related U.S. Application Data

(60) Division of application No. 11/810,685, filed on Jun. 6, 2007, now Pat. No. 8,118,789, which is a continuation-in-part of application No. 10/847,299, filed on May 18, 2004, now Pat. No. 7,270,653, and a continuation-in-part of application No. 10/371,395, filed on Feb. 20, 2003, now Pat. No. 7,276,056, which is a continuation-in-part of application No. 10/077,256, filed on Feb. 20, 2002, now Pat. No. 6,589,216.

(60) Provisional application No. 60/472,167, filed on May 21, 2003.

(51) Int. Cl.
*A61L 9/00* (2006.01)

(52) U.S. Cl. .......................................................... 422/5
(58) Field of Classification Search .................. 604/279, 604/515; 606/131; 422/5
See application file for complete search history.

(56) References Cited

FOREIGN PATENT DOCUMENTS

WO WO 2005115307 * 12/2005

OTHER PUBLICATIONS iSi, "The Odor Steeler from iSi North America", www.isinorthamerica.com/basics.htm, Mar. 19, 1999, p. 1.*

* cited by examiner

*Primary Examiner* — Matthew F Desanto

(57) ABSTRACT

A deodorizer device for controlling body odor comprises a structure having an external metal oxide surface with a contour to contact the surface of the skin where perspiration is produced and is degraded by bacterial organisms on the skin into body odor. The metal oxide surface is reactable with water supplied to the surface of the skin to render the bacterial organisms ineffectual to degrade perspiration later produced on the skin into body odor. The deodorizer device together with a water source form a deodorizer system. A method of controlling body odor involves supplying water to the surface of the skin where perspiration is produced and is degraded by bacterial organisms into body odor and, at the same time, contacting the surface of the skin with a metal oxide surface of a deodorizer device.

18 Claims, 6 Drawing Sheets

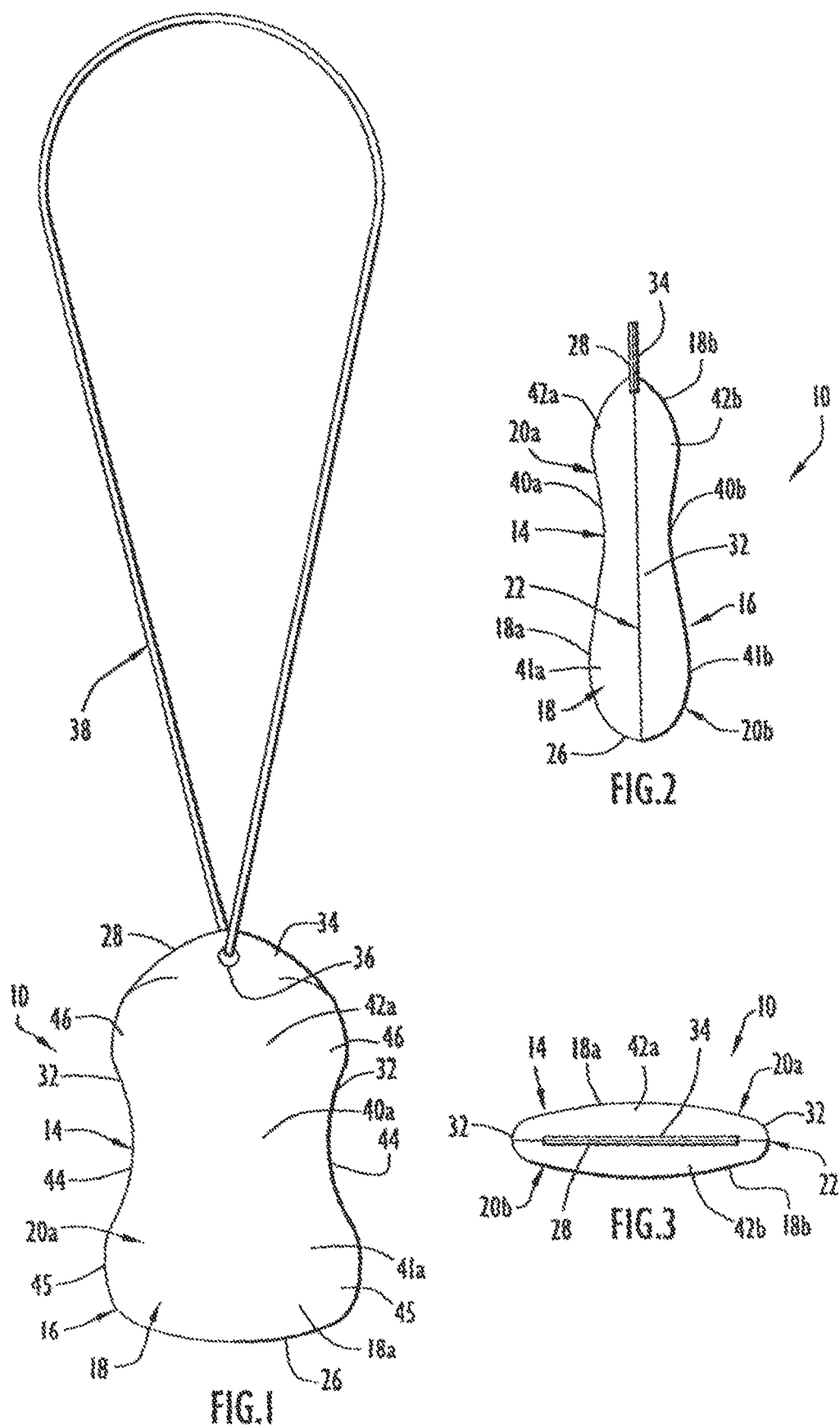

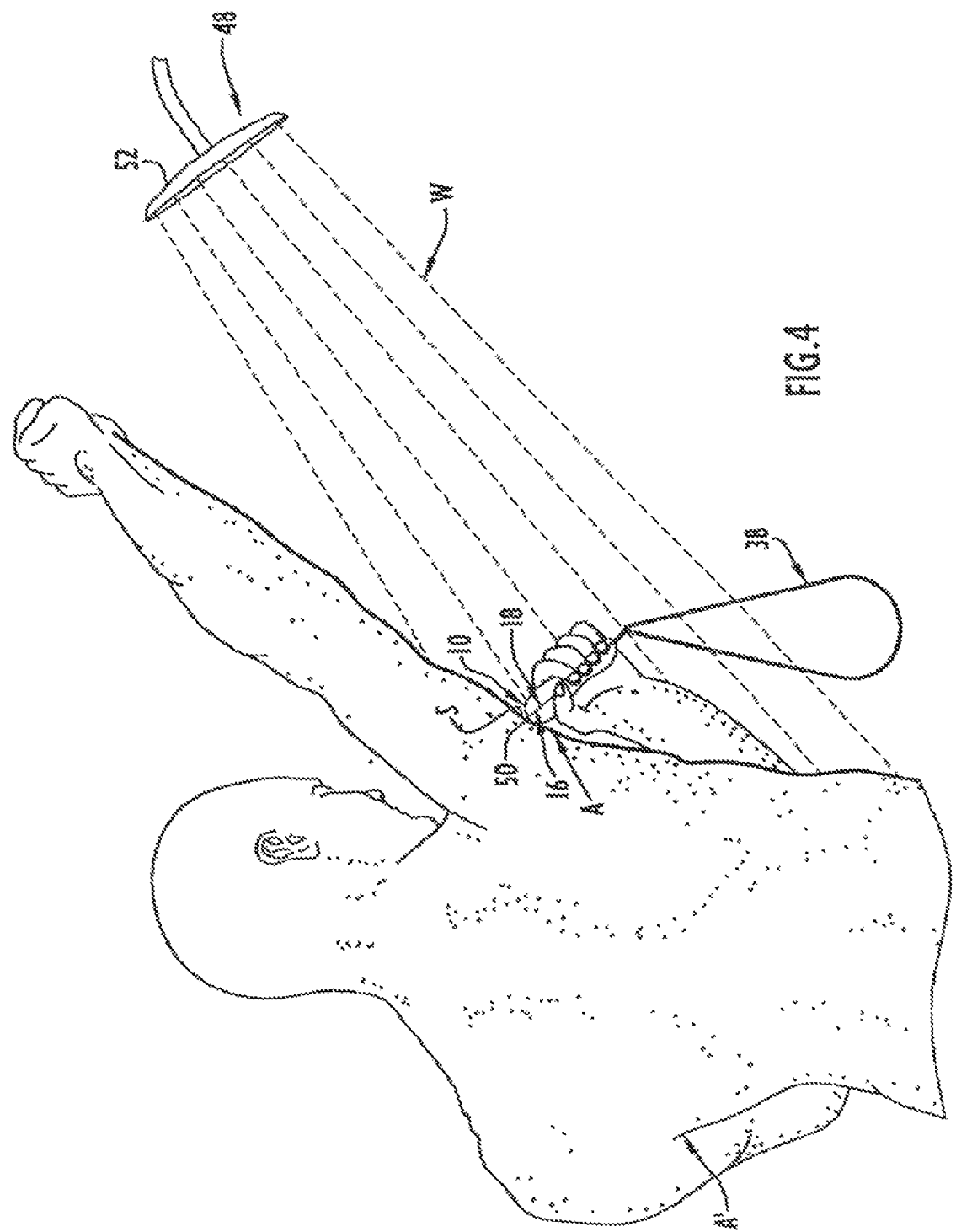

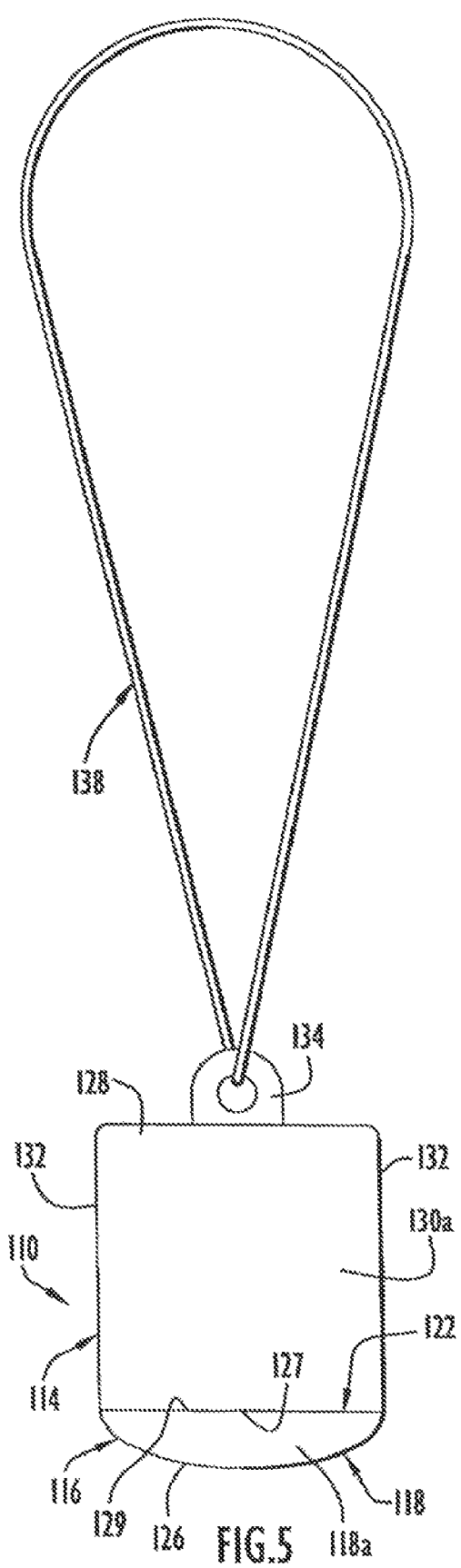
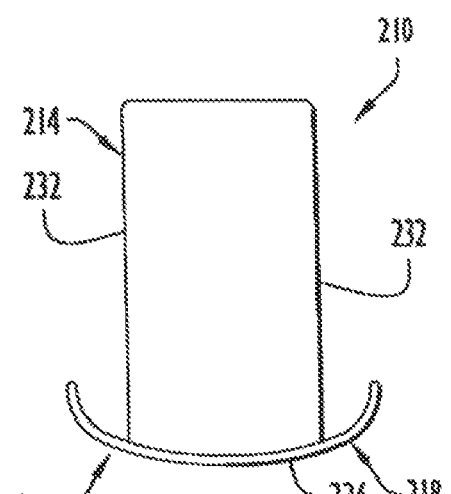
FIG.6
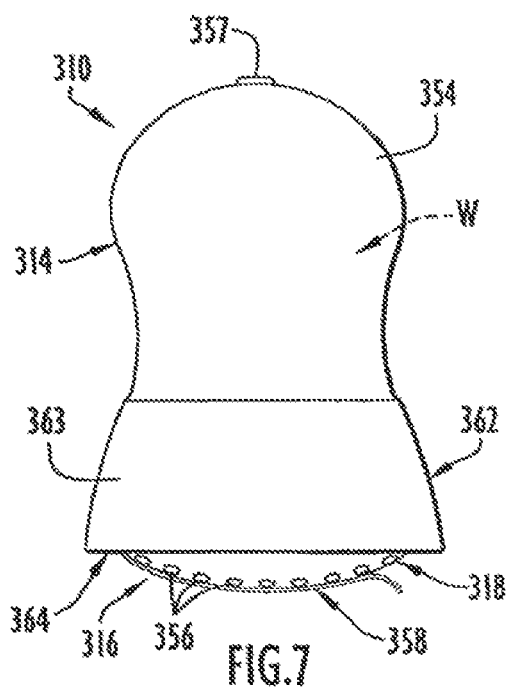
FIG.7
FIG.5

METHODS FOR CONTROLLING PERSPIRATION-RELATED BODY ODOR

CROSS-REFERENCE TO RELATED PATENT APPLICATIONS

This application is a divisional of prior U.S. patent application Ser. No. 11/810,685 filed Jun. 6, 2007, now U.S. Pat. No. 8,118,789 which is a continuation-in-part of prior U.S. patent application Ser. No. 10/847,299 filed May 18, 2004, now U.S. Pat. No. 7,470,653 claiming priority from provisional patent application Ser. No. 60/472,167 filed May 21, 2003. Prior U.S. patent application Ser. No. 10/847,299 is a continuation-in-part of prior U.S. patent application Ser. No. 10/371,395 filed Feb. 20, 2003, now U.S. Pat. No. 7,276,056 which is a continuation-in-part of prior U.S. patent application Ser. No. 10/077,256 filed Feb. 20, 2002 and now U.S. Pat. No. 6,589,216. The entire disclosures of all of the aforesaid patent applications are incorporated herein by reference.

BACKGROUND OF THE INVENTION

1. Field of the Invention

The present invention pertains to controlling body odor arising from the degradation or decomposition of perspiration produced by the skin. More particularly, the present invention pertains to devices, systems and methods for controlling body odor by deactivating bacterial organisms on the skin responsible for the degradation or decomposition of perspiration into body odor.

2. Brief Discussion of the Related Art

Various skin areas of the body contain sweat glands that produce perspiration, or sweat, on the surface of the skin. Various metabolic or biological processes play a role in the production of perspiration including temperature regulation, physical activity or exertion, emotional stress such as anger, fear and excitement, hormonal fluctuations, menopause, medicinal effects, and disease. Perspiration produced by the sweat glands appears on the surface of the epidermis, which constitutes the outermost layer of the skin. The sweat glands themselves are found in the reticular region of the dermis, the layer of the skin located just beneath the epidermis. Some skin areas of the body perspire more profusely than others, one reason being the higher density or concentration of sweat glands in some skin areas of the body. Furthermore, some skin areas of the body where perspiration is produced have only limited exposure to light and/or air due to their anatomical location and/or their being normally covered by clothing. The axillae, otherwise known as the underarms or armpits, and the feet are skin areas of the body where perspiration is produced, oftentimes profusely, and where there is typically minimal light and ventilation resulting in a damp environment. These skin areas present an environment especially favorable to the proliferation of various bacterial organisms that ordinarily colonize the surface of the epidermis and become mixed with the perspiration produced thereon. These organisms, including *Corynebacterium xerosis*, *Corynebacterium tuberculostearicum*, *Corynebacterium minutissimum*, *Staphylococcus epidermis*, *Staphylococcus haemolyticus* and *Bacillus licheniformis*, are not easily removable from the skin even by vigorous washing with soap and water. Soap and water are ineffective to deactivate the bacterial organisms ordinarily found on the skin, and these organisms even demonstrate a resistance to available antibiotics including penicillin and methycillin. Where the skin areas are not readily accessible due to their anatomical location and/or being covered by clothing, as is the case for the underarms and feet, perspiration produced on the skin surface during the course of a person's normal day typically cannot be dried, wiped or washed away soon after being produced. Furthermore, hairs growing from the skin surface, as is often the case for the underarms in particular, may act to trap or retain perspiration on or against the skin. Consequently, the perspiration produced on the skin of the underarms and feet will typically remain on and/or in contact with the skin surface for a considerable length of time, thusly creating the sustained damp or moist environment that is typical of the underarms and feet and that favors the proliferation of bacterial organisms. In addition to bacterial organisms, dead skin cells that continually slough off of the epidermis are normally present on the surface of the skin and become mixed with the perspiration produced thereon.

Although perspiration by itself is essentially an odorless fluid, the degradation or decomposition of perspiration by the bacterial organisms on the skin causes an offensive odor, commonly referred to as body odor, to be produced. Dead skin cells mixed in with the perspiration are also subject to degradation and decomposition by the bacterial organisms, and may exacerbate body odor. The underarms and feet provide an optimal environment for the production of body odor in that a larger population of bacterial organisms may be available to effect degradation or decomposition of perspiration, a greater quantity of perspiration may be available for degradation or decomposition by the bacterial organisms, degradation or decomposition of perspiration into body odor may occur at a faster rate due to the larger population of bacterial organisms and/or the greater quantity of perspiration, and/or degradation or decomposition of perspiration into body odor may occur over a longer period of time due to the conditions favorable to the production of body odor being sustained for relatively long periods of time. Although other skin areas of the body besides the underarms and feet produce perspiration, the hands being an example, they are not viewed as causing body odor due to such other skin areas producing a relatively minimal amount of perspiration, being more regularly exposed to light and/or air, and/or being more readily accessible for drying, wiping, washing or otherwise removing the perspiration therefrom soon after it is produced thereby presenting an environment not especially conducive to the degradation or decomposition of perspiration into body odor. Accordingly, the skin areas of the underarms and feet have become predominantly associated with body odor, i.e. the odor arising from the degradation or decomposition of perspiration produced by the skin. Odors having causes other than perspiration may emanate from the body but are not "body odor" because they do not arise from the degradation or decomposition of perspiration produced by and on the skin and, more particularly, from the degradation or decomposition of perspiration by bacterial organisms found on the skin. The mouth, the tongue, and the vaginal canal are examples of body areas that may emanate odors not related to or arising from skin perspiration.

Body odor is a great cause of concern for most individuals due to the adverse impact that body odor has on many aspects of a person's life. Individuals afflicted with body odor oftentimes experience various problems and disorders including social anxiety, social isolation or withdrawal, lack of confidence, embarrassment, humiliation, low self-esteem, shame, frustration, educational underachievement, employment difficulties and unsuccessful interpersonal relationships. In view of the widespread aversion to body odor and the fact that regular washing of the skin with soap and water does not effectively control body odor, various commercial deodorant products dedicated to controlling body odor have been proposed for use on the underarms and feet.

Commercial underarm deodorant products are typically chemically formulated substances provided in a medium allowing a layer, coating or film of the substance to be applied to the surface of the skin in the areas of the underarms. Commercial underarm deodorant products most commonly contain both a chemical anti-perspirant component and a chemical anti-odor component. Less commonly, commercial underarm deodorant products contain a chemical anti-odor component without an anti-perspirant component. The anti-perspirant components found in commercial underarm deodorant products use chemical agents to inhibit the production of perspiration on the surface of the skin. Commercial underarm deodorant products that have an anti-perspirant component thusly attempt to control body odor by reducing the amount of perspiration produced by and on the skin, but do not directly act on the underlying bacterial organisms responsible for degrading or decomposing the perspiration into body odor. The anti-perspirant components are oftentimes of limited effectiveness and the benefits derived therefrom are oftentimes of short duration. The anti-odor components found in commercial underarm deodorant products generally comprise chemical agents selected for their ability to diffuse odor. In many products, the anti-odor components attempt to absorb or merely mask the odor. Like the anti-perspirant components, the anti-odor components do not directly act on the underlying bacterial organisms responsible for degrading or decomposing perspiration into body odor. The anti-odor components, like the anti-perspirant components, oftentimes are of limited effectiveness and the benefits derived therefrom are oftentimes of short duration.

Because commercial underarm deodorant products are applied to the skin and are allowed to remain on the skin, it is possible for the chemical agents in the products to be absorbed by the body via the skin. Exposure to the chemical agents in underarm deodorant products is a cause of concern, especially in view of recent scientific evidence suggesting that the chemical agents used in commercial underarm deodorant products may be potentially harmful to humans. For example, many commercial underarm deodorant products contain aluminum which has been implicated in some scientific studies as a causative factor in Alzheimer's Disease and in cancer. The health risks associated with exposure to the chemical agents in underarm deodorant products may be exacerbated by the fact that underarm deodorant products are often copiously applied by individuals to their skin, the fact that the skin of the underarms is in close proximity to the axillary lymph nodes, the fact that underarm deodorant products are used by most individuals with regular frequency, i.e. usually at least once daily, the fact that underarm deodorant products typically remain on the skin for a significant length of time after being applied to the skin, and the fact that underarm deodorant products are used by most individuals over a major part of their lifetime. Despite potential health risks and the limited efficacy of commercial underarm deodorant products, such products remain widely used due to the stigma associated with body odor and the lack of viable alternatives to commercial underarm deodorant products.

Commercial foot deodorant products have many of the same disadvantages as commercial underarm deodorant products. In addition, the irregular anatomy of the feet makes it particularly difficult to apply foot deodorant products to the surface of the skin of the feet, especially the areas of and between the toes. Foot deodorant products are commonly provided as sprays or powders which are difficult to control during application and which are messy. Like commercial underarm deodorant products, commercial foot deodorant products attempt to control foot odor by reducing perspiration and/or by diffusing foot odor but do not address the issue of bacterial organisms responsible for degrading or decomposing perspiration on the feet into body odor.

Metal devices such as those called the Rub-A-Way and the OdorSteeler have been proposed for use in removing food odors, such as onion and garlic odors, from the hands. Unlike body odor, which results from perspiration produced by a person's body itself and from the degradation or decomposition of the perspiration by bacterial organisms on the person's skin, food odor is imparted to a person's hands as a result of direct contact with odoriferous foods. When the hands directly contact the odoriferous food, the odor of the food itself is transferred to the hands and may linger thereon for some time. The hands are the only skin areas of the body that would normally come into direct contact with odoriferous foods, and use of the aforementioned metal devices is thereby limited to the hands. Since the hands are not considered areas of the body where body odor is produced, the metal devices proposed for removing food odors from the hands are not relevant to the issue of body odor, which is an entirely different odor than food odor and which arises in different areas of the body than the hands.

Japanese Patent No. 2001186997A pertains to a device, formed mainly of stainless steel fibers of a specified diameter, for polishing and deodorizing the fingertips. The fibers provide an abrasive, textured or coarse surface for physically separating odor molecules from the skin so that the separated molecules can be washed away with water. The device relies on abrasion of the skin, which necessarily inflicts trauma to some extent. Use of the device on the fingertips shows it to be unrelated to body odor arising from perspiration.

U.S. Pat. No. 6,190,365 B1 and No. 6,589,216 B1 to Abbott et al disclose vaginal douche applicators with stainless steel surfaces for neutralizing odor in the vaginal canal. The vaginal odor to which the Abbott et al patents pertain is different from body odor that results from skin perspiration. The anatomical tissue within the vaginal canal is anatomically unlike the skin of the underarms and feet and does not contain sweat glands that produce perspiration.

SUMMARY OF THE INVENTION

The present invention is generally characterized in a deodorizer device for controlling body odor resulting from perspiration produced on the skin being degraded or decomposed by bacterial organisms on the skin. The deodorizer device is a structure having a grasping portion and a skin contacting portion. The grasping portion has a configuration to be grasped by the hand of a person using the deodorizer device. The skin contacting portion comprises an external surface of the structure having a contour to contact the surface of the skin where perspiration is produced and is degraded by bacterial organisms on the skin. The external surface is composed of metal oxide and is reactable with water supplied to the surface of the skin to render the bacterial organisms ineffectual to degrade perspiration later produced on the surface of the skin into body odor. The deodorizer device can be an underarm deodorizer device, with the external surface having a convexly curved contour to fit within the anatomical concavity of the underarm in contact with the concavely curved skin surface of the underarm. The deodorizer device can be a foot deodorizer device, with the external surface having a contour to contact the surface of the skin along the top, bottom and sides of the foot and between the toes of the foot.

The present invention is further generally characterized in a deodorizer system for controlling body odor resulting from perspiration produced on the skin being degraded or decomposed by bacterial organisms on the skin. The deodorizer system includes a source of water for being supplied to the surface of the skin where perspiration is produced and is degraded by bacterial organisms on the skin, and a deodorizer device having an external surface of metal oxide for being placed in contact with the surface of the skin that is supplied with the water from the water source. The deodorizer device comprises a structure having a grasping portion and a skin contacting portion. The grasping portion has a configuration to be grasped by the hand of a person using the deodorizer system. The skin contacting portion comprises the external surface of metal oxide, which has a contour to contact the surface of the skin supplied with water from the water source. The metal oxide external surface is reactable with the water supplied to the surface of the skin to render the bacterial organisms on the skin ineffectual to degrade perspiration later produced on the skin into body odor. The source of water can be external to the deodorizer device, or the source of water can be provided within the deodorizer device. The water can be ordinary tap water. The metal oxide external surface of the deodorizer device can have a convexly curved contour to fit within the anatomical concavity of the underarm in contact with the concavely curved skin surface of the underarm. The metal oxide external surface can have a contour to contact the surface of the skin along the top, bottom and sides of the foot and between the toes of the foot.

Additionally, the present invention is generally characterized in a method for controlling body odor arising from the degradation or decomposition of perspiration by bacterial organisms on the surface of the skin. The method involves the step of supplying water to the surface of the skin where perspiration is produced and is degraded by bacterial organisms on the surface of the skin into body odor, and the step of contacting the surface of the skin with a metal oxide surface of a deodorizer device to react with the water and render the bacterial organisms on the surface of the skin ineffectual to degrade perspiration later produced on the surface of the skin into body odor. The step of supplying water may involve supplying water from a source external to the deodorizer device or may involve supplying water from a source within the deodorizer device. The method may involve supplying the water to the surface of the skin of the underarm, contacting the surface of the skin of the underarm with the metal oxide surface of the deodorizer device to react with the water, and repeating the steps of supplying and contacting on the opposite underarm. The method may involve supplying the water to the surface of the skin of the foot, contacting the surface of the skin of the foot with the metal oxide surface of the deodorizer device to react with the water, and repeating the steps of supplying and contacting on the opposite foot. As part of the method, the steps of supplying and contacting may be repeated on a daily basis.

Various objects, advantages and benefits of the present invention will become apparent from the following description of preferred embodiments thereof taken in conjunction with the accompanying drawings wherein like reference numerals are used to designate like or similar parts.

BRIEF DESCRIPTION OF THE DRAWINGS

FIG. 1 is a top view of a deodorizer device of the present invention.

FIG. 2 is a side view of the deodorizer device.

FIG. 3 is a rearward end view of the deodorizer device.

FIG. 4 is a perspective view depicting a deodorizer system and method for controlling body odor using the deodorizer device.

FIG. 5 is a top view of an alternative deodorizer device.

FIG. 6 is a top view of a further alternative deodorizer device.

FIG. 7 is a top view of a self-contained deodorizer device forming a deodorizer system.

DESCRIPTION OF THE PREFERRED EMBODIMENTS

Figure 8:
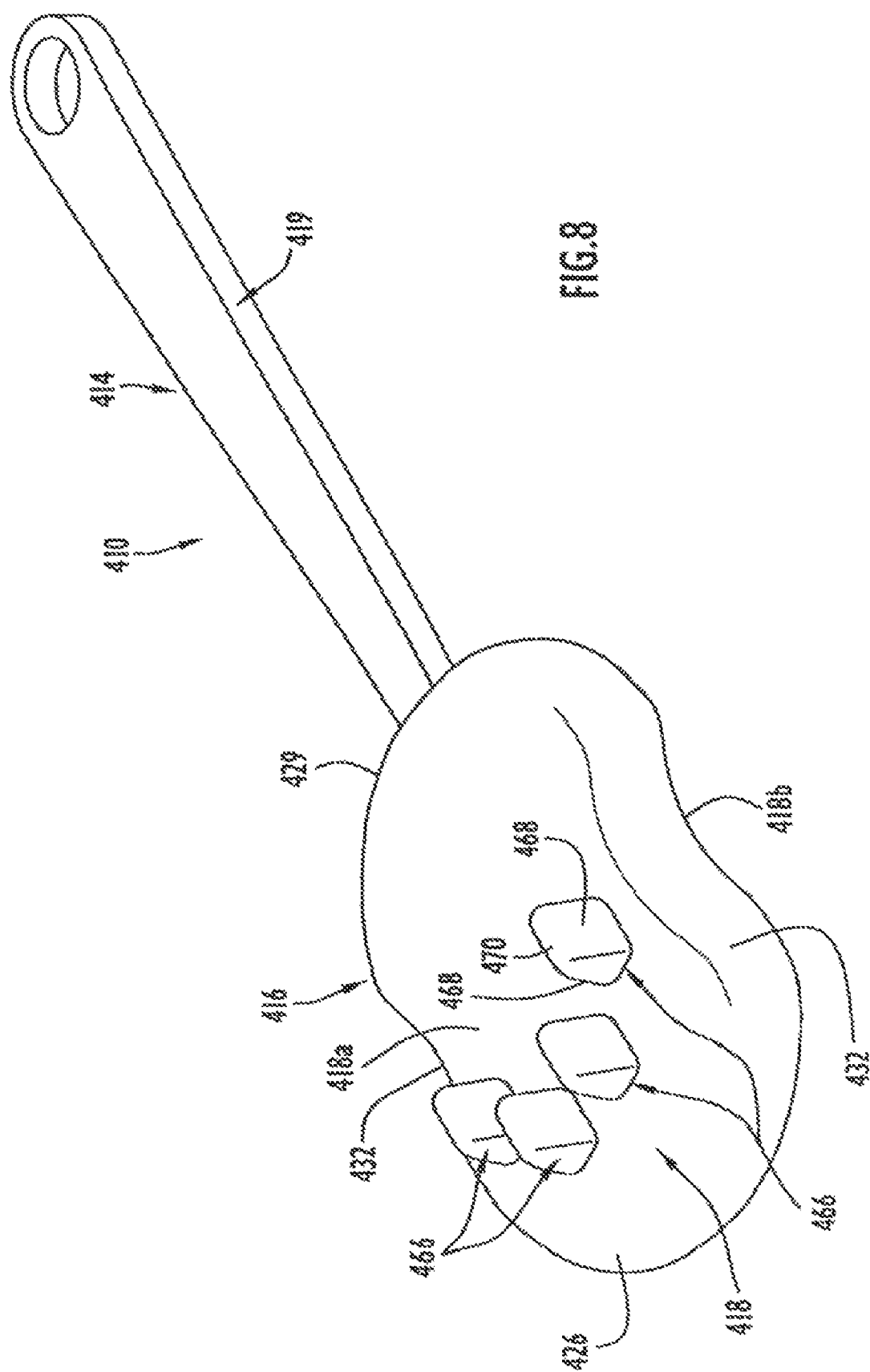
FIG. 8 is a perspective view of an additional deodorizer device.

A deodorizer device 10 for controlling body odor is depicted in FIGS. 1-3, the deodorizer device 10 being an underarm deodorizer device. The deodorizer device 10 is of a size and configuration to be grasped or held by a person in one hand to place a metal oxide surface of the deodorizer device in contact with the surface of the skin of the axilla area, commonly known as the underarm or armpit. The deodorizer device 10 is a structure having a grasping portion 14 with a configuration for being grasped or held by a person in the hand, and having a skin contacting portion 16 comprising an external surface 18 of metal oxide for being placed by the person in contact with the surface of the skin of the underarm.

The deodorizer device 10 can be fabricated integrally and unitarily or monolithically as a single structural component, in which case the single structural component defines or forms both the grasping portion 14 and the skin contacting portion 16 of the deodorizer device. Alternatively, the deodorizer device 10 can be fabricated of multiple, separate structural components assembled together to form the deodorizer device, as is the case for the deodorizer device 10. Where the deodorizer device 10 is made up of multiple assembled structural components, the grasping portion 14 and the skin contacting portion 16 may each be a separate structural component. Either or both of the grasping portion 14 and the skin contacting portion 16 can be fabricated integrally and unitarily or monolithically as a single structural component or as a plurality of separate structural components assembled together to form the grasping portion and/or the skin contacting portion. Where the deodorizer device 10 is made up of multiple assembled structural components, one or more of the multiple structural components can be fabricated integrally and unitarily or monolithically to define or form all or part of either or both of the grasping portion 14 and the skin contacting portion 16. As described further below, the deodorizer device 10 is representative of a structure composed of two assembled structural components, each structural component being an integral and unitary or monolithic component defining or forming part of the grasping portion 14 and part of the skin contacting portion 16.

The deodorizer device 10 comprises a first, top or upper structural component 20a and an identical or essentially identical second, bottom or lower structural component 20b assembled together in opposed facing relation to form the deodorizer device 10. Each structural component 20a and 20b is an integral and unitary or monolithic structural component and, when the structural components 20a and 20b are assembled to form the deodorizer device 10, a peripheral edge of the first structural component 20a meets or abuts a peripheral edge of the second structural component 20b along a junction or seam 22. The deodorizer device 10 has an outer or external surface comprising the outer or external surfaces of structural components 20a and 20b. The external metal oxide surface 18 of the skin contacting portion 16 is part of the outer surface of deodorizer device 10, and is formed in part by the external surface of structural component 20a and in part by the external surface of structural component 20b. The structural component 20a has an external surface of metal oxide defining a first, top or upper external metal oxide surface 18a of deodorizer device 10. The structural component 20b has an external surface of metal oxide defining a second, bottom or lower external metal oxide surface 18b of deodorizer device 10. Together the external metal oxide surfaces 18a and 18b comprise the external metal oxide surface 18 of the deodorizer device 10. The external metal oxide surfaces 18a and 18b of the structural components 20a and 20b are essentially continuous with one another due to there being minimal or no space between the peripheral edges of the structural components along the seam 22. Either or both of the structural components 20a and 20b can be made in their entirety of metal oxide. Alternatively, either or both of the structural components 20a and 20b can be comprised of a substrate or carrier made of any suitable material or materials other than metal oxide, with the external metal oxide surface 18a or 18b being formed of a layer of metal oxide disposed on the substrate or carrier. Either or both of the structural components 20a and 20b can be a relatively thin-walled component, in which case the deodorizer device 10 formed by the assembled structural components 20a and 20b may have a hollow or empty interior providing less weight and reduced material requirements compared to a solid structure.

The structural components 20a and 20b are secured in assembled relation to form the deodorizer device 10 and, preferably, the structural components 20a and 20b are secured in assembled relation in a permanent or essentially permanent manner. Any suitable securing means or mechanism can be used to secure the structural components 20a and 20b in assembled relation including a mechanical securing means or mechanism, composed of one or more mechanical securing elements, an adhesive securing means or mechanism, a heat seal securing means or mechanism, and/or a welded securing means or mechanism. The securing means or mechanism can be external and/or internal to the deodorizer device 10, but it is preferred that an external securing means or mechanism not obtrude visually and tactilely with the continuity of the external surfaces 18a and 18b at or along the seam 22 and that it not interfere with establishing direct contact between the surface of the skin and the external metal oxide surface 18 of the deodorizer device as described further below. The securing means or mechanism will most typically be located at, near or along the seam 22 and, where the deodorizer device 10 has a hollow interior, the securing means or mechanism can also serve to provide a seal along the seam 22 to prevent the entry of fluid into the interior of the deodorizer device 10. Alternatively, a dedicated seal can be provided in or on the deodorizer device 10 apart from the securing means or mechanism.

A mechanical securing means or mechanism for deodorizer device 10 can comprise one or more mechanical securing elements, each securing element being composed of a pair of interengaging locking formations on the structural components 20a and 20b. For example, structural component 20a can have a locking formation that lockingly interengages with a locking formation of structural component 20b to form a mechanical securing element. Locking formations of various configurations and designs can be provided on the structural components 20a and 20b to lockingly interengage in a permanent or essentially permanent manner. The mechanical securing means or mechanism can comprise one or more mechanical securing elements, each formed of a pair of interengaged locking formations either external or internal to the deodorizer device 10. Furthermore, it should be appreciated that the mechanical securement provided by a mechanical securing means or mechanism can be reinforced or supplemented using another form of securement such as an adhesive securing means or mechanism, a heat seal securing means or mechanism, and/or a welded securing means or mechanism between the structural components 20a and 20b. Also, it should be appreciated that the structural components 20a and 20b can have portions that overlap or nest together in assembled relation.

The outer or external surface of deodorizer device 10 defines an external configuration having top surface 18a, bottom surface 18b, an arcuate or rounded forward end 26, a rearward end 28 opposite the forward end 26, and opposed sides 32. The deodorizer device 10 is an example of one that has a length between its forward end 26 and its rearward end 28 that is greater than its width between the opposed sides 32. The width of the deodorizer device 10 is greater than the height of the deodorizer device 10 between its top surface 18a and its bottom surface 18b. The forward end 26 of the deodorizer device 10 is arcuate or rounded with a convex curvature between the sides 32, and is defined in part by the top surface 18a and in part by the bottom surface 18b. The rearward end 28 may be arcuate or rounded and, in the case of deodorizer device 10, the rearward end 28 is arcuate or rounded with a convex curvature between the sides 32, but comprises a flat tab 34 of reduced thickness having a hole 36 therethrough for attachment of a hanger 38 to the deodorizer device 10. The rearward end 28, including tab 34, is formed in part by the top surface 18a and in part by the bottom surface 18b.

The top surface 18a of deodorizer device 10 is configured to have a first, top or upper concave indentation or depression 40a situated between a first, top or upper convex forward hump 41a and a first, top or upper convex rearward hump 42a. The bottom surface 18b of deodorizer device 10 is configured similar to the top surface 18a and has a second, bottom or lower concave indentation or depression 40b situated between a second, bottom or lower convex forward hump 41b and a second, bottom or lower convex rearward hump 42b. The top and bottom forward and rearward humps 41a, 41b and 42a, 42b have a convex curvature in the longitudinal (front to rear) and lateral (side to side) directions as best seen from FIGS. 2 and 3. The top and bottom concave depressions 40a, 40b may have a concave curvature in the longitudinal and lateral directions. The sides 32 of deodorizer device 10 are each configured to have a side concave indentation or depression 44 situated between a side forward bulge 45 and a side rearward bulge 46. The side concave depressions 44 may have a concave curvature in the longitudinal direction and from top to bottom. The side forward and rearward bulges 45 and 46 can be convexly curved in the longitudinal direction and from top to bottom. The top and bottom concave depressions 40a and 40b are aligned with the side concave depressions 44 along the length of the deodorizer device 10, and together the top and bottom concave depressions 40a and 40b and the side concave depressions 44 comprise a narrowed region of the grasping portion 14 located between widened or broadened forward and rearward end regions of the deodorizer device 10. The narrowed region in conjunction with the widened rearward end region, formed by the top and bottom rearward humps 42a and 42b and side rearward bulges 46, provide a configuration for being comfortably grasped by a person in one hand while the widened forward end region, formed by the top and bottom forward humps 41a and 41b and side forward bulges 45, remains at least substantially uncovered by the hand and exposed. The widened forward and rearward end regions also act to deter slippage of the deodorizer device 10 from the hand. It is preferred that the external configuration of deodorizer device 10 be smooth and without any sharp edges, corners or points so as to avoid inflicting trauma or injury on a person during use of the deodorizer device.

The hanger 38 may be designed in any suitable way to allow the deodorizer device 10 to be suspended or hung from a conveniently located fixture or structure when not being used and/or to be suspended or hung from the hand of a person when carrying the deodorizer device. Since the deodorizer device 10 will ordinarily be used in a bathroom, the hanger 38 can be designed to allow the deodorizer device 10 to be suspended or hung from a hook, a faucet or any other conveniently available permanent or non-permanent fixture or structure typically found or used in a bathroom. The hanger 38 is shown by way of example as a rope or cord forming a closed loop passing through the hole 36 and made of a water-resistant, water-tolerant, water-proof, or water-repellent material. The loop can be placed over an available fixture or structure to hang the deodorizer device 10 therefrom and can be draped over the fingers and grasped with the hand to carry the deodorizer device 10. Moreover, the loop can be made of sufficient length to be placed over the head and worn around the neck to allow the deodorizer device 10 to be suspended from the neck hands-free.

The skin contacting portion 16 of the deodorizer device 10 may be comprised of any part of the external metal oxide surface 18 that the person is able to place in contact with the surface of the skin of the underarm while grasping the deodorizer device via the grasping portion 14. In the case of deodorizer device 10, the forward end 26, the top forward hump 41a, the bottom forward hump 41b, and the side forward bulges 45 will normally be uncovered or substantially uncovered by the hand used to grasp the grasping portion 14 and may be used to contact the skin of the underarm. The external metal oxide surface 18 along the forward end 26, the top forward hump 41a and/or the bottom forward hump 41b will most typically be used as the skin contacting portion 16 for the deodorizer device 10, although it should be appreciated that other areas of the external metal oxide surface 18 can be used as the skin contacting portion 16. The convex curvatures of the forward end 26 and of the humps 41a, 41b provide the skin contacting portion 16 with a contour to facilitate or maximize direct contact with the surface of the skin of the underarm. In particular, the convex curvatures of the forward end 26 and of the humps 41a, 41b are able to fit within the anatomical concavity of the underarm in a complementary manner and to conform to the concave curvature of the skin surface of the underarm. The external metal oxide surface 18 that forms the skin contacting portion 16 is a smooth, solid surface of manufactured or finished metal. The external surface 18 is preferably made of stainless steel, and the metal oxide of external surface 18 is preferably the metal oxide that is present and contained in the external surface of stainless steel as a product or result of its manufacture in accordance with conventionally known processes of stainless steel manufacture. It should be appreciated, however, that various metal oxides can be used for external surface 18 including those based on chromium, titanium, copper, and silver, and that the external surface 18 does not have to be made of stainless steel. The deodorizer device 10 is one in which the external surface 18 is stainless steel.

The deodorizer device 10 is used by a person to control body odor, particularly underarm body odor, arising from perspiration produced by and on the skin and from the degradation or decomposition of the perspiration by bacterial organisms on the skin. In the areas of the underarms, it is normal for sweat glands in the skin to produce perspiration or sweat that appears on the surface of the skin and, more specifically, on the surface of the epidermis constituting the outer layer of the skin. Various metabolic or biological processes that play a role in the production of perspiration include temperature regulation, physical activity or exertion, emotional stress such as anger, fear and excitement, hormonal fluctuations, menopause, medicinal effects, and disease. The amount of perspiration produced by and on the skin of the underarms will ordinarily vary during the course of a person's day. Essentially every person experiences some underarm perspiration. Most people at times experience heavy underarm perspiration, and many people regularly perspire profusely in the areas of the underarms. The anatomical location of the underarms and the fact that the underarms are usually covered by clothing greatly limit the extent to which the skin of the underarms is exposed to light and/or air. Hairs growing from the surface of the skin of the underarms may also act to trap or retain perspiration on or in contact with the skin surface. Consequently, the underarms present a damp or moist environment in which perspiration produced by the skin tends to remain on or in contact with the surface of the skin. Practical considerations of daily life ordinarily make it unfeasible for a person to dry, wipe or wash the skin of the underarms to remove perspiration therefrom soon after the perspiration is produced. Given that most people shower or bathe once or twice a day, it is most typical for underarm perspiration to remain in situ between showers or baths and for the damp or moist conditions of the underarms to be sustained for relatively long periods of time.

Although perspiration by itself does not have an offensive odor, the offensive odor known as body odor is produced as a result of perspiration being degraded or decomposed by bacterial organisms found on the surface of the skin. Bacterial organisms that may be found on the surface of the skin include *Corynebacterium tuberculostearicum, Corynebacterium minutissimum, Staphylococcus epidermis, Staphylococcus haemolyticus* and *Bacillus licheniformis*. These bacterial organisms can be tenacious and are not effectively removed by washing with soap and water, as well as being resistant to many antibiotics. The sustained damp or moist conditions and the lack of light and air that are typical of the underarms are especially favorable for the proliferation of the bacterial organisms on the skin of the underarms. The bacterial organisms become mixed with the perspiration on the skin surfaces of the underarms and act to degrade or decompose the perspiration into body odor. Skin cells that are regularly sloughed off of the epidermis of the skin of the underarms may also become mixed with underarm perspiration and degraded or decomposed by the bacterial organisms, which further contributes to and exacerbates the production of body odor.

A method for controlling body odor using deodorizer device 10 is depicted in FIG. 4 and is carried out using water W supplied from a water source 48 external to the deodorizer device 10. The deodorizer device 10 and the water W supplied from water source 48 comprise a deodorizer system for controlling body odor. The method will typically be performed in a bathroom, washroom or other area having an available water source associated with a structure for collecting and draining water, such as a shower, tub or sink. Most typically, the method will be performed as part of the person's normal regimen for cleansing or washing the body, such as a shower, bath or other cleansing or washing regimen. However, it should be appreciated that the method can be performed independently, apart from the person's normal cleansing or washing regimen. The water W is ordinary tap water, and the water source 48 can be any conveniently available source of ordinary tap water such as a plumbing system having a shower head, nozzle or faucet from which the water W is discharged. In the method depicted in FIG. 4, the source 48 of water W is a plumbing system having a shower head 52 from which the water W is discharged in a conventional manner.

As shown in FIG. 4, the person using the deodorizer device 10 grasps the grasping portion 14 in one hand so that the skin contacting portion 16 can be placed by the person into direct contact with the surface 50 of the skin S of the underarm A. When the grasping portion 14 of the deodorizer device 10 is grasped by the person in one hand, the external stainless steel or metal oxide surface 18 along forward end 26 and along the top and bottom forward humps 41a and 41b is available to be placed into direct contact with the surface 50 of the skin S of the underarm A. Typically the deodorizer device 10 will be held and manipulated using the hand and arm opposite the arm associated with underarm A. The person raises the arm associated with underarm A to expose the surface 50 of the skin S of the underarm A to the water W being discharged from the shower head 52. With the surface 50 of the skin S of the underarm A positioned to receive the flow of water W thereon, the opposite arm and hand holding the deodorizer device 10 is/are manipulated as needed to bring the skin contacting portion 16, i.e. the external stainless steel or metal oxide surface 18, into direct contact with the surface 50 of the skin S of the underarm A. The external stainless steel or metal oxide surface 18 is moved along the skin surface 50 of the underarm A by further manipulating the arm and/or hand while maintaining the external surface 18 in direct contact with the skin surface 50 and while continuing to expose the skin surface 50 to the flow of water W. In order to achieve good direct contact with the skin surface 50, the external surface 18 can be pressed against the skin surface 50 using gentle pressure or force, with the resiliency of the skin S causing the surface 50 thereof to conform to the external surface 18. The external surface 18 is moved along the skin surface 50 while being held in direct contact therewith so that the skin surface of the entire underarm A is subjected to both the flow of water W and, simultaneously therewith, direct contact with the external stainless steel or metal oxide surface 18. The deodorizer device 10 can be moved in any direction and/or can be oriented to face in any direction convenient and comfortable for the person to move the external surface 18 along and in contact with the skin surface 50 of the entire underarm A. The deodorizer device 10 can, for example, be moved longitudinally, laterally or in any other direction along the skin surface 50 of the underarm A. During the procedure, the external surface 18 can be lifted away from the skin surface 50, thusly breaking direct contact therewith, and reoriented and/or repositioned on the skin surface 50 to reestablish direct contact therewith as needed to subject the skin surface 50 of the entire underarm A to the water W and the simultaneous direct contact with the external stainless steel or metal oxide surface 18. During the procedure, the skin surface 50 will most typically be contacted with the external surface 18 along the forward end 26, the top forward hump 41a and/or the bottom forward hump 41b. However, it should be appreciated that any portion of the external stainless steel or metal oxide surface 18 can be used to directly contact the skin surface 50. The convex curvatures of the forward end 26 and of the top and bottom forward humps 41a and 41b facilitate and maximize direct contact between the external surface 18 and the surface 50 of the skin S of the underarm A in that the convex curvatures fit or nestle within the anatomical concavity of the underarm and conform or are complementary to the concave curvature of the skin surface 50. Movement of the external surface 18 along and in direct contact with the skin surface 50 of the entire underarm A in the presence of the water W can be repeated or overlapped several times for maximum effectiveness. Once the procedure has been performed on the underarm A, it is repeated on the skin surface of the opposite underarm A'.

The external stainless steel or metal oxide surface 18 in direct contact with the skin surface 50 of the underarm A reacts with the water W supplied to the skin surface to create a reaction by which bacterial organisms on the skin surface 50 are deactivated or rendered ineffectual to degrade or decompose perspiration later produced on the skin surface 50 into body odor, thereby retarding the production of body odor. The reaction produced by the stainless steel or metal oxide in contact with the skin surface 50 in the presence of the water W attacks and is believed to kill bacterial organisms on the skin surface 50 including one or more of *Corynebacterium xerosis, Corynebacterium tuberculostearicum, Corynebacterium minutissimum, Staphylococcus epidermis, Staphylococcus haemolyticus* and *Bacillus licheniformis*. Accordingly, when perspiration later occurs on the skin surface 50, there are fewer or no active bacterial organisms present to degrade or decompose the perspiration (as well as sloughed off skin cells) into body odor, and body odor is thereby controlled. The reaction achieved with the deodorizer device 10 does not rely on chemical anti-perspirant agents intended to inhibit perspiration, on chemical anti-odor agents intended to diffuse or mask odor, or on abrasives that attempt to physically separate or remove organisms from the skin. The deodorizer device 10 and the deodorizer system and method for controlling body odor using the deodorizer device 10 thusly avoids exposing the person to potentially harmful chemical substances and the health risks associated with exposure to chemical substances, and avoids abrasion of the skin. When performed on a regular basis at least once daily, the method for controlling body odor using deodorizer device 10 can control body odor in the underarms A, A' in a manner equivalent to or better than the control obtained from commercial underarm deodorant products without the potential health risks.

An alternative deodorizer device 110 is depicted in FIG. 5. The deodorizer device 110 is a structure having a grasping portion 114 fabricated as a separate individual structural component and having a skin contacting portion 116 also fabricated as a separate individual structural component, with the separate individual structural components being assembled together to form the deodorizer device 110. Also, the outer or external surface of the deodorizer device 110 is composed of a material other than metal oxide along the grasping portion 114 and is composed of metal oxide along the skin contacting portion 116. As an example, the external or outer surface of the grasping portion 114 can be made of plastic, and the grasping portion 114 can be made in its entirety of plastic or another material other than metal oxide. The grasping portion 114 includes the tab 134 extending from its rearward end which constitutes the rearward end 128 of the deodorizer device 110. The grasping portion 114 is fabricated, for example by molding, as an integral and unitary or monolithic structural component. However, it should be appreciated that the grasping portion 114 could be composed of a plurality of separate individual structural components assembled together to form the grasping portion 114. The skin contacting portion 116 is fabricated as an integral and unitary or monolithic structural component but could be composed of a plurality of separate structural components assembled together to form the skin contacting portion 116.

The skin contacting portion 116 can have a dome-like configuration with an external metal oxide surface 118 that meets or abuts the external surface of the grasping portion 114 along a seam or junction 122. In the case of deodorizer device 110, the external surface 118 is stainless steel. The skin contacting portion 116 can be made in its entirety of stainless steel or metal oxide, or just the external surface 118 of the skin contacting portion can be made of stainless steel or metal oxide. The external surface of the grasping portion 114 and the external stainless steel or metal oxide surface 118 of the skin contacting portion 116 together define or form the outer surface of the deodorizer device 110. The deodorizer device 110 thusly differs from deodorizer device 110 in that the outer surface of deodorizer device 110 is not made in its entirety of stainless steel or metal oxide. Rather, the outer surface of deodorizer device 110 is stainless steel or metal oxide along the external surface of the skin contacting portion 116 but not along the external surface of the grasping portion 114.

The grasping portion 114 and the skin contacting portion 116 can be secured together in assembled relation in any suitable way. For example, the grasping portion 114 can be fabricated with an open forward end 127, and the skin contacting portion 116 can have a neck secured within the open forward end 127 of the grasping portion 114. When the grasping portion 114 and the skin contacting portion 116 are assembled to form the deodorizer device 110, a peripheral edge of the grasping portion 114 meets or abuts a peripheral edge of the skin contacting portion 116 at the seam or junction 122. The external surface of the grasping portion 114 can be essentially continuous with the external surface of the skin contacting portion 116, i.e. surface 118, at or along the seam 122 due to there being minimal or no gap between the peripheral edge of the grasping portion 114 and the peripheral edge of the skin contacting portion 116 at seam 122.

The grasping portion 114 has a top surface 130a, a bottom surface (not visible in FIG. 5) opposite the top surface 130a, the forward end 127, the rearward end 128 opposite the forward end 127, and opposed sides 132 extending from the forward end 127 to the rearward end 128. The bottom surface of the grasping portion 114 can be the same as or similar to the top surface 130a. The sides 132 of the grasping portion 114 can be parallel between forward end 127 and rearward end 128. The grasping portion 114 can have an oval, elliptical, oblong, circular or any suitable cross-sectional configuration between the seam 122 and the rearward end 128. The cross-sectional configuration of the grasping portion 114 can be uniform or constant from the seam 122 to the rearward end 128. The skin contacting portion 116 has top surface 118a, a bottom surface (not visible in FIG. 5) opposite the top surface 118a, a forward end that defines the forward end 126 of the deodorizer device 110, and a rearward end 129 joined to the forward end 127 of grasping portion 114. The top surface 118a is preferably convexly curved in the lateral direction between the sides 132 and in the longitudinal direction between the forward end 126 and the rearward end 129. The bottom surface of the skin contacting portion 116 can be the same as or similar to the top surface 118a. The forward end 126 is arcuate or rounded with a convex curvature in the lateral direction between sides 132. The external stainless steel surface 118 of the skin contacting portion 116 can meet and be essentially continuous with the external surface of the grasping portion 114 at the seam 122. A hanger 138, such as a rope or cord, can be attached to the tab 134 as described above for the deodorizer device 10.

The deodorizer device 110 and a supply of water from an external water source form a deodorizer system for controlling body odor, and underarm odor in particular, as described above for the deodorizer device 10. A method for controlling body odor, and underarm odor in particular, using the deodorizer device 110 is similar to that described above for deodorizer device 10. The person using the deodorizer device 110 will ordinarily grasp the deodorizer device 110 along the grasping portion 114 with one hand and will contact the skin surface of the underarm with the external stainless steel or metal oxide surface 118 of the skin contacting portion 116 while simultaneously exposing the skin surface to water.

FIG. 6 illustrates a further alternative deodorizer device 210. The deodorizer device 210 is similar to the deodorizer device 110 except that the skin contacting portion 216 of deodorizer device 210 comprises a thin sheet of material affixed to the forward end 227 of the grasping portion 214 with the sides of the skin contacting portion 216 extending laterally beyond the sides 232 of the grasping portion 214. The grasping portion 214 can be the same as or similar to the grasping portion 114. The skin contacting portion 216 presents the convexly curved external stainless steel or metal oxide surface 218 at the forward end 226 of the deodorizer device 210. The deodorizer device 210 is an example of one in which the outer or external surface of the skin contacting portion 216 is not essentially continuous with the outer or external surface of the grasping portion 214 due to the skin contacting portion 216 extending laterally and protruding beyond the sides 232 of the grasping portion 214. The deodorizer device 210 is depicted without a hanger, however, it should be appreciated that the deodorizer device 210 can be provided with a hanger attached to the grasping portion 214 or another suitable location on the deodorizer device. The deodorizer device 210 and a supply of water from an external water source form a deodorizer system for controlling body odor, and underarm odor in particular, as explained above. Use of the deodorizer device 210 in a method for controlling body odor, and underarm odor in particular, is essentially like that described above for deodorizer devices 10 and 110.

A deodorizer device 310 that is capable of serving as a self-contained deodorizer system, without requiring an external water source, is illustrated in FIG. 7. The grasping portion 314 for deodorizer device 310 comprises an enclosure or water reservoir 354 having an interior for holding a supply or quantity of water W. The skin contacting portion 316 for deodorizer device 310 is similar to the skin contacting portion 116 but has one or more holes or apertures 356 therein along the external stainless steel or metal oxide surface 318 in communication with the interior of the water reservoir 354. The skin contacting portion 316 is illustrated as having a plurality of holes 356 distributed along the external surface 318. The grasping portion 314 is preferably made partly or entirely of a deformable or flexible material such that the grasping portion 314 can be manually squeezed to cause the water W within the water reservoir 354 to be discharged through the holes 356. The grasping portion 314 is depicted as having a narrowed region between widened forward and rearward end regions to facilitate grasping and squeezing of the grasping portion 314 with one hand The skin contacting portion 316 may be a dome-like structural component attached to an open forward end of the grasping portion 314. The grasping portion 314 can be provided with a removable and replaceable plug 357, allowing the water reservoir 354 to be filled with water W prior to use and/or allowing it to be refilled with water W for repeated use of the deodorizer device 310.

Of course, the deodorizer device 310 can be designed to be disposable after a single use, and the reservoir 354 can be designed to be non-refillable.

In order to prevent discharge of the water W through the one or more holes 356 when the deodorizer device 310 is not in use, a removable cover, lid, seal or cap 358 can be provided on the skin contacting portion 316 over the one or more holes 356. As an example, FIG. 7 depicts the cover 358 as a sheet of material releasably adhesively secured on the external surface 318 to cover and seal holes 356 and prevent the release of water W through the holes 356. By using a releasable adhesive to attach the sheet of material to the external surface 318, the sheet of material can be manually peeled away from the external surface 318 to expose the holes 356 as shown in FIG. 7 in order to permit water W in reservoir 354 to be discharged from holes 356 during use of the deodorizer device 310. Of course, it should be appreciated that the cover 358 can be designed in various other ways including snap-on, screw-on and hinged lids or caps. The deodorizer device 310 may comprise a collector 362 for collecting the water discharged from the one or more holes 356 during use of the deodorizer device 310. The collector 362 is depicted by way of example in FIG. 7 as a collar 363 having a narrow end attached to the grasping portion 314 and having a wider open end adjacent or close to the external surface 318 at the forward end of the deodorizer device 310. The collar 363 can have a funnel-like configuration around the skin contacting portion 316, with the collar 363 flaring outwardly from its narrow end to its wider open end. The collar 363 defines a collection chamber 364 around the skin contacting portion 316 for collecting water W that is discharged from the one or more holes 356 during use of the deodorizer device 310.

Since the deodorizer device 310 has a source of water W that is internal to the deodorizer device 310, the deodorizer device 310 comprises in itself a deodorizer system. In a method for controlling body odor, and underarm odor in particular, using the deodorizer device 310 and system, the person using the device grasps the grasping portion 314 in one hand and uses the opposite hand to remove the cover 358 and expose the holes 356. Where the cover 358 is a sheet of material as illustrated for deodorizer device 310, the cover 358 can be removed by peeling the sheet of material away from the external surface 318. Where the deodorizer device 310 is designed to be disposable after a single use, the cover 358 can be discarded once it has been removed. Where the deodorizer device 310 is designed to be reusable, the cover 358 should be retained in order to be replaced on the skin contacting portion 316 following use of the deodorizer device 310.

Once the holes 356 are uncovered or exposed, the person manipulates the deodorizer device 310 to bring the external stainless steel or metal oxide surface 318 into contact with the surface of the skin of the underarm as described above for deodorizer devices 10, 110 and 210. With the external stainless steel or metal oxide surface 318 in contact with the skin surface, the hand grasping the grasping portion 314 is used to squeeze the grasping portion 314 to effect release or discharge of water W in reservoir 354 from the holes 356. Accordingly, the surface of the skin is subjected to contact with the external stainless steel or metal oxide surface 318 and, at the same time, to a flow of water W discharged from the holes 356 along the external surface 318. The skin surface of the entire underarm is contacted with the external stainless steel or metal oxide surface 318 at the same time that water W is supplied to the skin surface as described above in connection with the use of deodorizer devices 10, 110 and 210, and the procedure is repeated on the opposite underarm. During the procedure, water that is released from the holes 356 into contact with the surface of the skin is collected in the collection chamber 364. If necessary, the collection chamber 364 can be emptied during the course of the procedure. The reservoir 354 will preferably be provided with a sufficient quantity of water to carry out the procedure on the skin surfaces of both underarms. After carrying out the procedure on both underarms, the deodorizer device 310 can be disposed of if it is designed for a single use. Where the deodorizer device 310 is designed to be reusable, the reservoir 354 can be refilled with water prior to the next use and, if the reservoir 354 will contain water between uses, the cover 358 can be replaced on the skin contacting portion 316 to prevent water from being discharged from the holes 356 between uses. The self-contained deodorizer device 310 offers the benefit of being able to carry out the method for controlling body odor when an external source of water is not available.

An additional deodorizer device 410 is depicted in FIG. 8, the deodorizer device 410 being a foot deodorizer device. The deodorizer device 410 is a structure comprising a grasping portion 414 and a skin contacting portion 416. The skin contacting portion 416 comprises a structural component having an external stainless steel or metal oxide surface 418, and the grasping portion 414 comprises a structural component configured in the form of a handle 419 attached to the skin contacting portion 416. The skin contacting portion 416 can be fabricated integrally and unitarily or monolithically as a single member or part, or can be fabricated of multiple members or parts assembled together to form the skin contacting portion 416. The external stainless steel or metal oxide surface 418 defines an external configuration for the skin contacting portion 416 having a top surface 418*a*, a bottom surface 418*b*, a forward end 426, a rearward end 429, and opposed sides 432. In addition, the external configuration of skin contacting portion 416 includes a plurality of toe insert elements 466. The toe insert elements 466 can be provided at any suitable location on the skin contacting portion 416, and are provided by way of example on the top surface 418*a* of skin contacting portion 416. Four toe insert elements 466 are shown in FIG. 8 as being provided on the top surface 418*a* of the skin contacting portion 416. The toe insert elements 466 have a configuration and are arranged on the skin contacting portion 416 for insertion between adjacent toes of the foot. The toe insert elements 466 each have a length or longitudinal dimension extending longitudinally or lengthwise along the skin contacting portion 416 in parallel with each other, and each toe insert element 466 comprises opposed side surfaces 468 extending along the length of the toe insert element. The side surfaces 468 of each toe insert element 466 extend from the top surface 418*a* angularly inwardly toward each other to a rounded tip 470 of the toe insert element. Accordingly, each toe insert element 466 has a tapered cross-sectional configuration from the top surface 418*a* to its tip 470 to facilitate insertion of the toe insert element 466, tip 470 first, between adjacent toes of the foot. In addition, the toe insert elements 466 are arranged on the top surface 418*a* at spaced locations to facilitate their insertion between the adjacent toes of the foot. At least the side surfaces 468 of the toe insert elements 466 are external stainless steel or metal oxide surfaces, and preferably the entire external surface of each toe insert element 466 is part of the external stainless steel or metal oxide surface 118. It is preferred that the skin contacting portion 416 and its toe insert elements 466 be without any sharp edges, points or corners. The external stainless steel or metal oxide surface 418 including the toe insert elements 466 is shaped or contoured to maximize contact of the external stainless steel or metal oxide surface 418 with the skin surface of the foot. The handle 419 is attached to the rearward end 429 of the skin contacting portion 416, and can have any suitable configuration for being grasped in one hand by the person using the deodorizer device 410 and can be of appropriate length to facilitate manipulation of the skin contacting portion 416 to place the external stainless steel or metal oxide surface 418 into contact with the skin surface of the foot.

Figure 9:
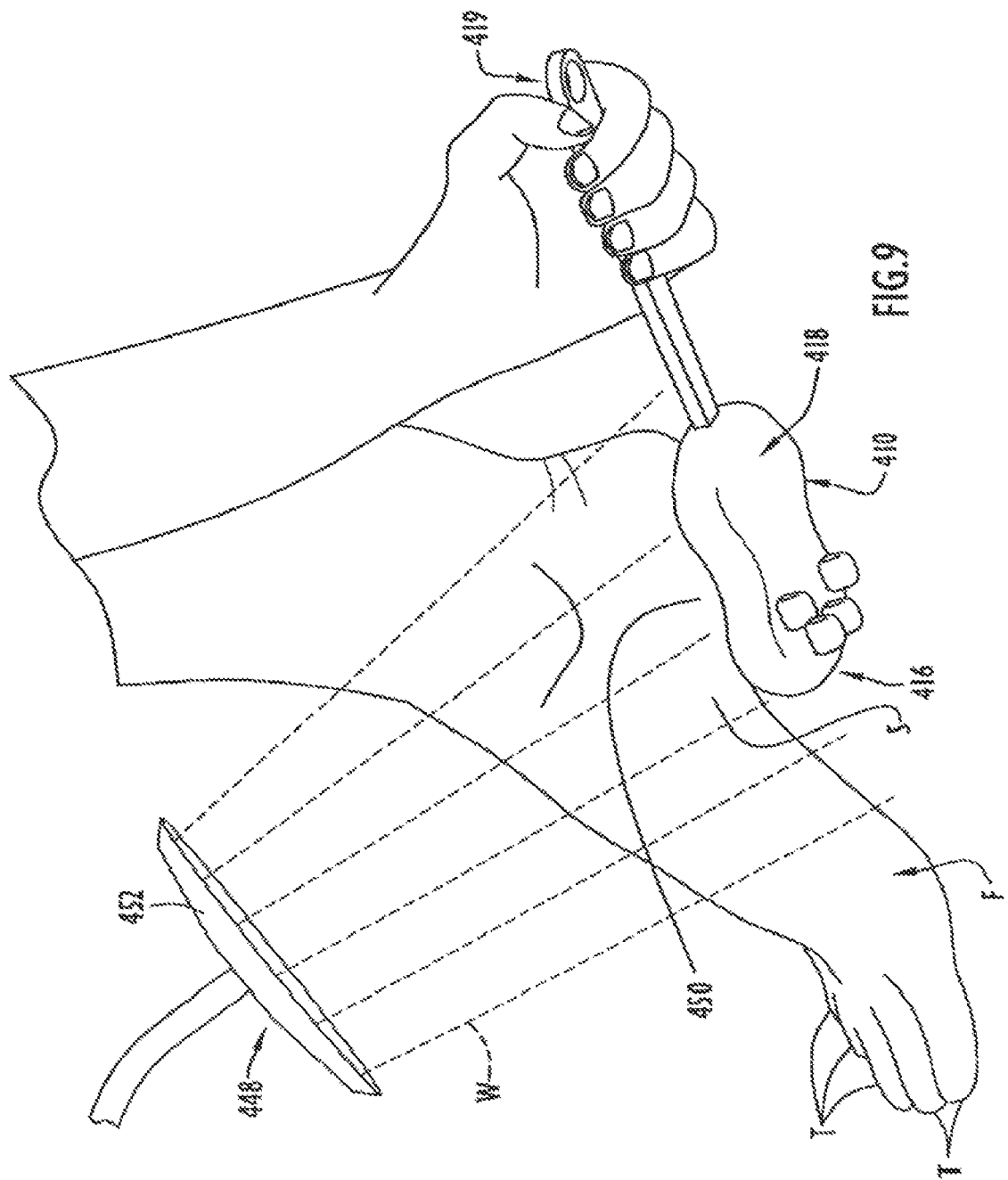
FIG. 9 is a perspective view depicting another deodorizer system and method for controlling body odor using the deodorizer device of FIG. 8.
Figure 10:
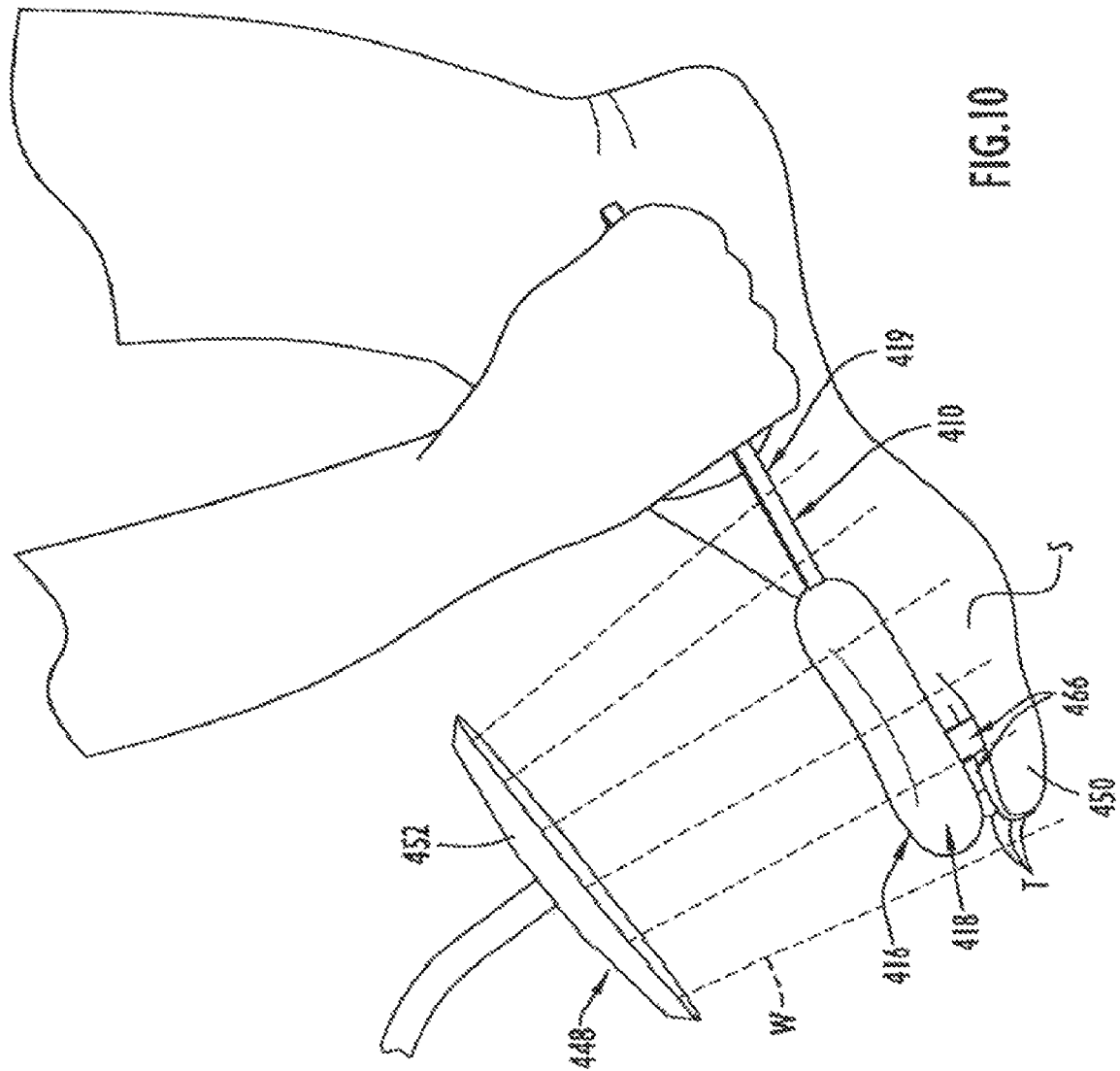
FIG. 10 is a perspective view depicting an alternative or additional step in the method for controlling body odor using the deodorizer device of FIG. 8.

The deodorizer device 410 is used with water supplied from an external water source. Together the deodorizer device 410 and the water supplied from the water source comprise a deodorizer system. Of course, it should be appreciated that the deodorizer device 410 can be designed with an internal water source in a manner similar to deodorizer device 310 to provide a self-contained foot deodorizer device and foot deodorizer system. FIGS. 9 and 10 illustrate a method for controlling body odor, and foot odor in particular, using the deodorizer device 410. The deodorizer device 410 is used in a manner similar to that described above for deodorizer device 10, and the external stainless steel or metal oxide surface 418 of the deodorizer device 410 is brought into contact with the surface 450 of the skin S of a foot F in the presence of water W. A person using the deodorizer device 410 grasps the handle 419 in one hand and manipulates the skin contacting portion 416 as needed to bring the external surface 418 into direct contact with the surface 450 of the skin S of the foot F. FIG. 9 shows the external surface 418 along the bottom surface 418b of the skin contacting portion 416 in direct contact with the surface 450 of the skin S along the bottom or sole of the foot F while, at the same time, water W is supplied to the skin surface 450 being contacted with the external stainless steel or metal oxide surface. FIG. 9 depicts the water W being supplied from an external water source 448 such as a shower head 452 of a plumbing system. The external stainless steel or metal oxide surface 418 of the skin contacting portion 416 along the bottom surface 418b, or any other portion of the external stainless steel or metal oxide surface 418, can be used to contact the surface 450 of the skin S. The external stainless steel or metal oxide surface 418 is moved along the surface 450 of the skin S while at the same time exposing the skin surface 450 to the water W until the skin surface of the entire foot F, or as much thereof as possible, has been subjected to both contact with the metal oxide of external surface 418 and the water W. The same portion of the external surface 418 used to contact the bottom of the foot F can be used to contact the skin surface 450 along the top and sides of the foot F. In order to contact the skin surface 450 in the areas between adjacent toes T of the foot F, the toe insert elements 466 are utilized as shown in FIG. 10. The toe insert elements 466 are inserted, tips 470 first, between adjacent toes T of the foot F, with the tapered configuration of the toe insert elements 466 facilitating their insertion by gently separating the toes T. The side surfaces 468 of each toe insert element 466 will contact the skin surface 450 along the sides of the adjacent toes T to maximize contact between the skin surface 450 and the external stainless steel or metal oxide surface 418. The skin contacting portion 416 can be manipulated by the person via the handle 419 to move the toe insert elements 466 back and forth longitudinally, laterally and/or rotatably between the toes. At the same time that the skin surface 450 between the toes T is contacted with the external stainless steel or metal oxide surface 418 of the toe insert elements 466, water W is supplied thereto as shown in FIG. 10. The procedure is repeated on the opposite foot. Contact of the skin surfaces of the feet with the external stainless steel or metal oxide surface 418 of the deodorizer device 410 in the presence of water W results in a reaction that causes bacterial organisms on the skin S to be deactivated or rendered ineffectual to degrade or decompose perspiration later produced on the skin surfaces of the feet in the same manner as described above for controlling underarm odor.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method for controlling body odor arising from the degradation of perspiration by bacterial organisms on the surface of the skin, comprising the steps of
supplying water to the surface of the skin of an underarm where perspiration is produced and is degraded by bacterial organisms on the surface of the skin of the underarm into body odor;
contacting the surface of the skin of the underarm, as it is being supplied with the water, with a metal oxide surface of a metal deodorizer device to react with the water and render the bacterial organisms on the surface of the skin of the underarm ineffectual to degrade perspiration later produced on the surface of the skin of the underarm into body odor; and
repeating said steps of supplying and contacting on the opposite underarm.

2. The method for controlling body odor recited in claim 1 and further including the steps of supplying water to the surface of the skin of a foot where perspiration is produced and is degraded by bacterial organisms on the surface of the skin of the foot into body odor, contacting the surface of the skin of the foot, as it is being supplied with the water, with the metal oxide surface of the deodorizer device to react with the water and render the bacterial organisms on the surface of the skin of the foot ineffectual to degrade perspiration later produced on the surface of the skin of the foot into body odor, and repeating said steps of supplying and contacting on the opposite foot.

3. The method for controlling body odor recited in claim 2 wherein said step of contacting the surface of the skin of the foot includes contacting the surface of the skin between the toes of the foot.

4. The method for controlling body odor recited in claim 1 wherein said step of supplying water includes supplying water from a water source external to the deodorizer device.

5. The method for controlling body odor recited in claim 1 wherein said step of supplying water includes supplying water from a water reservoir within the deodorizer device.

6. The method for controlling body odor recited in claim 1 and further including the step of performing said steps of supplying, contacting and repeating daily.

7. The method for controlling body odor recited in claim 1 wherein said step of contacting includes contacting the surface of the skin of the underarm with a stainless steel surface of the deodorizer device.

8. A method for controlling body odor arising from the degradation of perspiration by bacterial organisms on the surface of the skin, comprising the steps of
supplying plain tap water to the surface of the skin of an underarm where perspiration is produced and is degraded by bacterial organisms on the surface of the skin of an underarm into body odor;
contacting the surface of the skin of the underarm, as it is being supplied with the water, with a metal oxide surface of a metal deodorizer device to react with the water and render the bacterial organisms on the surface of the skin of the underarm ineffectual to degrade perspiration later produced on the surface of the skin of the underarm into body odor;

repeating said steps of supplying and contacting on the opposite underarm; and performing said steps of supplying, contacting and repeating at least once daily on a regular basis.

9. The method for controlling body odor recited in claim 8 and further including the steps of supplying plain tap water to the surface of the skin of a foot where perspiration is produced and is degraded by bacterial organisms on the surface of the skin of the foot into body odor, contacting the surface of the skin of the foot, as it is being supplied with water, with a metal oxide surface of a foot deodorizer device to react with the water and render the bacterial organisms on the surface of the skin of the foot ineffectual to degrade perspiration later produced on the surface of the skin of the foot into body odor, and repeating said steps of supplying and contacting on the opposite foot.

10. The method for controlling body odor recited in claim 9 wherein said step of contacting the surface of the skin of the foot includes contacting at least substantially the entire surface of the skin of the foot.

11. The method for controlling body odor recited in claim 10 wherein said step of contacting the surface of the skin of the foot includes inserting toe insertion elements of the foot deodorizer device between adjacent toes of the foot.

12. The method for controlling body odor recited in claim 9 wherein said step of supplying water to the surface of the skin of a foot includes positioning the foot to receive a flow of water from a shower nozzle.

13. The method for controlling body odor recited in claim 8 wherein said step of supplying includes positioning the underarm to receive a flow of water from a shower nozzle.

14. The method for controlling body odor recited in claim 8 wherein said step of contacting includes contacting at least substantially the entire surface of the skin of the underarm.

15. A method for controlling body odor arising from the degradation of perspiration by bacterial organisms on the surface of the skin, comprising the steps of subjecting the surface of the skin of the underarm area on one side of the body to a flow of water discharged from a shower nozzle;

contacting the surface of the skin of the underarm area on the one side of the body, as it is simultaneously being subjected to the flow of water, with a metal oxide surface of a hand-held metal deodorizer device to react with the water and render the bacterial organisms on the surface of the skin of the one underarm area ineffective to degrade perspiration later produced on the surface of the skin into body odor;

repeating said steps of subjecting and contacting on the surface of the skin of the underarm area on the opposite side of the body; and performing said steps of subjecting, contacting and repeating at least once daily on a regular basis to control underarm odor without the need for soap and chemical underarm deodorant and antiperspirant products.

16. The method for controlling body odor recited in claim 15 wherein said step of contacting includes pressing the metal oxide surface of the deodorizer device against the surface of the skin.

17. The method for controlling body odor recited in claim 16 wherein said step of contacting includes moving the metal oxide surface of the deodorizer device along the surface of the skin to cover at least substantially the entire underarm areas.

18. The method for controlling body odor recited in claim 17 wherein said step of moving includes overlapping areas of contact between the metal oxide surface of the deodorizer device and the surface of the skin of the underarm areas.

* * * * *